(12) United States Patent
Akiyama et al.

(10) Patent No.: US 12,025,558 B2
(45) Date of Patent: Jul. 2, 2024

(54) FRESHNESS LABEL WITH AGGREGATION-INDUCED PHOSPHOR

(71) Applicant: TOSHIBA TEC KABUSHIKI KAISHA, Tokyo (JP)

(72) Inventors: Ryozo Akiyama, Mishima Shizuoka (JP); Yukitami Mizuno, Ota Tokyo (JP); Kazuki Taira, Ota Tokyo (JP)

(73) Assignee: Toshiba Tec Kabushiki Kaisha, Tokyo (JP)

( * ) Notice: Subject to any disclaimer, the term of this patent is extended or adjusted under 35 U.S.C. 154(b) by 858 days.

(21) Appl. No.: 16/931,126

(22) Filed: Jul. 16, 2020

(65) Prior Publication Data

US 2021/0140887 A1    May 13, 2021

(30) Foreign Application Priority Data

Nov. 12, 2019  (JP) .................. 2019-205060

(51) Int. Cl.
*G01N 31/22* (2006.01)
*B65D 25/02* (2006.01)
(Continued)

(52) U.S. Cl.
CPC ......... *G01N 21/6428* (2013.01); *B65D 25/02* (2013.01); *G01N 21/77* (2013.01);
(Continued)

(58) Field of Classification Search
CPC .... G01N 21/6428; G01N 21/77; G01N 31/22; G01N 33/02; G01N 2021/6432;
(Continued)

(56) References Cited

U.S. PATENT DOCUMENTS

2006/0240565 A1  10/2006  Tang et al.
2015/0268204 A1   9/2015  Akiyama et al.
(Continued)

FOREIGN PATENT DOCUMENTS

CN  107807113 A  3/2018
JP  2012-051816 A  3/2012
(Continued)

OTHER PUBLICATIONS

Mitsutaka Nakamura et al., "Fluorometric Sensing of Biogenic Amines with Aggregation-Induced Emission-Active Tetraphenylethienes", Chemistry: A European Journal, 2011, 17, pp. 5344-5349.

(Continued)

*Primary Examiner* — David P Porta
*Assistant Examiner* — Mamadou Faye
(74) *Attorney, Agent, or Firm* — Kim & Stewart LLP (57) ABSTRACT

A freshness label in an embodiment includes a base material having a fluid retention capacity and a phosphor layer on a surface of the base material. The phosphor layer includes an aggregation-induced phosphor. The base material has a porous or mesh structure. The aggregation-induced phosphor comprises a phosphor having a polar functional group or the like. The freshness label can be used to detect spoilage and/or deterioration of fresh food according to changed in fluorescence intensity provided by the aggregation-induced phosphor.

10 Claims, 6 Drawing Sheets

(51) Int. Cl.
   *G01N 21/64* (2006.01)
   *G01N 21/77* (2006.01)
   *C07H 21/02* (2006.01)
   *G01N 33/02* (2006.01)

(52) U.S. Cl.
   CPC ............ *G01N 31/22* (2013.01); *C07H 21/02* (2013.01); *G01N 2021/6432* (2013.01); *G01N 2021/6439* (2013.01); *G01N 2021/7786* (2013.01); *G01N 33/02* (2013.01)

(58) Field of Classification Search
   CPC ... G01N 2021/6439; G01N 2021/7786; G01N 33/533; G01N 33/543; G01N 33/525; G01N 21/64; B65D 25/02; C07H 21/02; C09K 11/06; C09K 11/025; C09K 2211/1007; C09K 2211/1096
   See application file for complete search history.

(56) References Cited

U.S. PATENT DOCUMENTS

| | | | |
|---|---|---|---|
| 2017/0160270 A1 | 6/2017 | Iwanaga et al. | |
| 2017/0307579 A1* | 10/2017 | Akiyama | ............ G01N 33/521 |
| 2018/0067087 A1* | 3/2018 | Akiyama | ............ G01N 33/68 |
| 2018/0209950 A1* | 7/2018 | Iwanaga | ............ C09B 23/148 |

FOREIGN PATENT DOCUMENTS

| | | |
|---|---|---|
| JP | 2016-158587 A | 9/2016 |
| JP | 2017-058233 A | 3/2017 |
| JP | 2017-102104 A | 6/2017 |

OTHER PUBLICATIONS

Extended European Search Report dated Mar. 22, 2021 mailed in corresponding European Patent Application No. 20203530.9, 8 pages.

Meng Gao et al: "Fluorescent Light-Up Detection of Amine Vapors Based on Aggregation-Induced Emission", ACS Sensors, vol. 1, No. 2, Dec. 8, 2015 (Dec. 8, 2015), pp. 179-184, XP055548230, ISSN: 2379-3694, DOI: 10.1021/acssensors.5b00182.

Parvej Alam et al: "A Highly Sensitive Bimodal Detection of Amine Vapours Based on Aggregation Induced Emission of 1,2-Dihydroquinoxaline Derivatives", Chemistry a European Journal, vol. 23, No. 59, Aug. 10, 2017 (Aug. 10, 2017), pp. 14911-14917, XP055548246, DE, ISSN: 0947-6539, DOI: 10.1002/chem.201703253.

Notice of Reasons for Refusal dated Aug. 1, 2023 in corresponding Japanese Patent Application No. 2019-205060, 6 pages (with Translation).

* cited by examiner

$$\text{K VALUE (\%)} = \frac{\text{HxR} + \text{Hx}}{\text{ATP} + \text{ADP} + \text{AMP} + \text{IMP} + \text{HxR} + \text{Hx}} \times 100$$

| | INITIAL DRY STATE (FLUORESCENT STATE) | AFTER IMMERSION IN PURE WATER (WATER QUENCHING STATE) | AFTER 1h |
|---|---|---|---|
| STEAM EXPOSURE TO ACETATE WATER | ● | ● | ● |
| STEAM EXPOSURE TO PURE WATER ONLY | ● | ● | ● |

FRESHNESS LABEL WITH AGGREGATION-INDUCED PHOSPHOR

CROSS-REFERENCE TO RELATED APPLICATION

This application is based upon and claims the benefit of priority from Japanese Patent Application No. 2019-205060, filed on Nov. 12, 2019, the entire contents of which are incorporated herein by reference.

FIELD

Embodiments described here relate generally to a freshness label.

BACKGROUND

Fresh food such as seafood products, fruits and vegetables, and livestock products have poor storage properties at room temperature and are perishable. Therefore, a method for evaluating freshness is in demand. As methods for evaluating freshness of fresh food, there are various methods such as a sensory evaluation method, a chemical evaluation method, a physical evaluation method, and a microbiological method. The sensory evaluation method is a method for evaluating fresh food using the appearance, smell, and tactile sensation such as firmness. The chemical evaluation method is based on gas chromatography-mass spectrometry (GC-mass spec or GC-MS) of chemical components generated due to deterioration or spoilage of fresh food, or liquid chromatography-mass spectrometry (LC-MS) of nucleic acid-related compounds or the like. The physical evaluation method is an evaluation method based on various physical indices of fresh food, such as rigidity index (RI value), breaking strength, texture, and impedance. The microbiological method is a method for examining the number of general viable bacteria, spoilage bacteria, pathogenic bacteria, or the like, contained in fresh food.

The sensory evaluation method can be employed to evaluate the freshness in a short time without requiring an expensive measuring device, but has a problem that a result varies depending on an evaluator. The chemical evaluation method, the physical evaluation method, and the microbiological method are less likely to involve a variation in a result by an evaluator, but may not be easily performed due to requirement of devices or equipment and may require time for measurement, in some cases. That is, simplicity or accuracy is sacrificed, in the sensory evaluation method, the chemical evaluation method, the physical evaluation method, and the microbiological method.

To address the problem, a freshness label using an aggregation-induced phosphor has been proposed. With such a freshness label, freshness of food can be evaluated by measuring a fluorescence intensity of the label. Here, the aggregation-induced phosphor is a compound that shows aggregation-induced emission (AIE). The aggregation-induced phosphor shows weak fluorescence or no fluorescence when each molecule is dissolved in a solution such as a soluble organic solvent. The dissolved (non-aggregated state) molecules of the aggregation-induced phosphor, react with a chemical component released due to spoilage or deterioration of fresh food and thus aggregate to form an aggregate. It is the aggregate that emits strong fluorescence. The aggregation-induced phosphor is preferably designed in a structure having a functional group that reacts with a spoilage component (or a component generate by spoilage or decay). For example, if an amine component, which is one possible spoilage component, is used as the target component for the aggregation-induced phosphor, the aggregation-induced phosphor preferably has a carboxylic acid group as functional group.

DETAILED DESCRIPTION

An embodiment described herein is directed to providing a freshness label capable of confirming freshness of food with convenience and high accuracy, A chemical structure of a marker for a freshness label is disclosed.

According to an embodiment, a freshness label is described. The freshness label includes a label base material that retains fluid and a phosphor layer on an outer surface of the label base material. The phosphor layer includes an aggregation-induced phosphor.

According to another embodiment, a method for presenting a freshness level of a food product with a freshness label is described. The method includes immersing the freshness label in an aqueous solution, and after the immersing, packing the food product along with the freshness label in a container.

To address the presented problem(s) associated with freshness determinations, a freshness label using an aggregation-induced phosphor has been proposed. With such a freshness label, freshness of food can be evaluated by measuring a fluorescence intensity of the label. Here, the aggregation-induced phosphor is a compound that shows aggregation-induced emission (AIE). The aggregation-induced phosphor shows weak fluorescence or no fluorescence when each molecule is dissolved in a solution such as a soluble organic solvent. The dissolved (non-aggregated state) molecules of the aggregation-induced phosphor, react with a chemical component released due to spoilage or deterioration of fresh food and thus aggregate to form an aggregate. It is the aggregate that emits strong fluorescence.

The aggregation-induced phosphor is preferably designed in a structure having a functional group that reacts with a spoilage component (or a component generate by spoilage or decay). For example, if an amine component, which is one possible spoilage component, is used as the target component for the aggregation-induced phosphor, the aggregation-induced phosphor preferably has a carboxylic acid group as functional group.

The present inventors conducted intensive studies and found that a freshness label containing aggregation-induced phosphor required improvements in accuracy and performance. That is, existing freshness label containing an aggregation-induced phosphor dissolved in an organic solvent were only placed in proximity with fresh food within a sealed container having the fresh food therein. The fresh food is a food with a high water content, generally. Therefore, it was assumed considered that water vapor pressure in the sealed container would reach a saturated water vapor pressure over time. Since the aggregation-induced phosphor in these labels is a water-insoluble substance, and it was assumed the aggregation-induced phosphor would hardly be affected by water in this context. However, the present inventors found that as the water vapor pressure in the container increases, fluorescence of the freshness label weakens. That is, a fluorescence intensity of the freshness label is affected by water in the gas phase. Therefore, in an environment with gradually increasing humidity, an influence of chemical components released due to the spoilage or degradation of the fresh food is not accurately reflected in the fluorescence intensity. The example embodiment described herein is based on such findings.

The structure for a freshness label according to an embodiment includes a label base material (also referred to as a base material) and a phosphor layer. The phosphor layer includes an aggregation-induced phosphor fixed to the base material. The structure for a freshness label contains the aggregation-induced phosphor in a solid state, and thus shows strong fluorescence.

Figure 1:
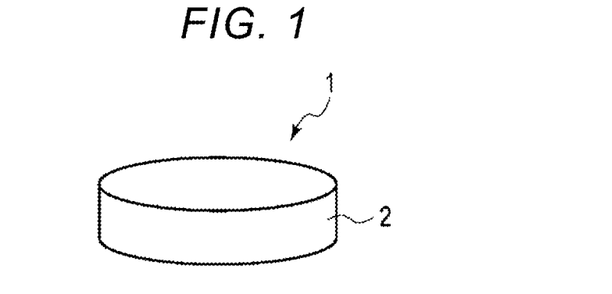
FIG. 1 schematically illustrates a perspective view of a structure for a freshness label according to an embodiment.
Figure 2:
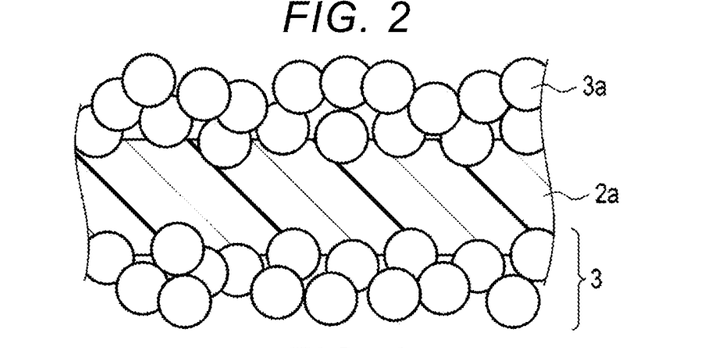
FIG. 2 schematically illustrates an enlarged cross-sectional view of the structure for a freshness label.

FIG. 1 schematically illustrates a perspective view of a structure for a freshness label according to an embodiment. A freshness label material 1 (referred to also as a structure 1 for a freshness label or more simply as structure 1) shown in FIG. 1 includes a base material 2 and a phosphor layer (not separately depicted in FIG. 1). FIG. schematically illustrates an enlarged cross-sectional view of the structure for a freshness label shown in FIG. 1. The structure 1 for a freshness label shown in FIGS. 1 and 2 is an example using filter paper as the base material 2. A phosphor layer 3 is supported on a fiber 2a of the base material 2. The phosphor layer 3 thus comprises an aggregation-induced phosphor 3a fixed to the fiber 2a of the base material 2.

The base material 2 is not limited to any particular shape (or dimension) or material, as long as the base material 2 can be impregnated with water (e.g., absorb water or permit percolation/flow of water). The base material 2 is, for example, a porous body or a mesh structure. The shape of the base material 2 may be circular as shown in FIG. 1 or may be polygonal. The thickness of the base material 2 is, for example, 0.1 mm or more and 1.0 mm or less. The thickness of the base material 2 is not particularly limited, as long as a detectable amount of fluorescence emitted from the aggregation-induced phosphor can be provided. Also, any thickness of the base material is sufficient, unless the reaction between the aggregation-induced phosphor and the spoiled component inside the base material is hindered due to too large thickness.

The base material 2 includes, for example, a synthetic fiber, an inorganic fiber, a natural fiber, or a mixture thereof. Examples of the synthetic fiber include a polyolefin-based fiber and a cellulosic fiber. Examples of the inorganic fiber include a glass fiber, a metal fiber, an alumina fiber, and an activated carbon fiber. Examples of the natural fiber include wood pulp and hemp pulp. The base material 2 is preferably a layer including a glass fiber.

The phosphor layer 3 contains the aggregation-induced phosphor 3a, and preferably includes only the aggregation-induced phosphor 3a. The phosphor layer 3 is supported on the base material 2. The phosphor layer 3 is preferably supported on the surface (e.g., outer surface) of the fiber 2a or the like of the base material 2, in a thin layer.

The thickness of the phosphor layer 3 is preferably such that if the phosphor layer 3 is allowed to stand in an environment at 25° C. and 100% relative humidity, the fluorescence intensity of the phosphor layer 3 will be substantially reduced. Here, the expression "the fluorescence intensity of the phosphor layer 3 is substantially reduced" refers to a detectable or otherwise appreciable change in fluorescence intensity over time. For example, if a fluorescence intensity obtained by allowing the phosphor layer 3 to equilibrate in an environment at 10° C. and 20% relative humidity is considered to be 100% value/level, then the fluorescence intensity obtained by allowing the phosphor layer 3 to equilibrate in the environment at 25° C. and 100% relative humidity is calculated as a relative value with respect to the 100% intensity value/level, the fluorescence intensity obtained by allowing the phosphor layer 3 to stand in the environment at 25° C. and 100% relative humidity would be a value/level of 30% or less. The fluorescence intensity is measured using, for example, a photodetector such as a photodiode, or an image pickup device such as a complementary metal-oxide-semiconductor (CMOS) image sensor and a charge-coupled device (CCD) image sensor. If a color-type image pickup device is used, for example, an average of RBG gradation values can be used as the fluorescence intensity.

The thickness of the phosphor layer 3 can affect the fluorescence intensity of the freshness label. That is, if the phosphor layer 3 is thickened, the fluorescence intensity of the freshness label tends to increase. On the other hand, if the phosphor layer 3 is excessively thick, then the change in the fluorescence intensity resulting from a change in freshness becomes small. The thickness of the phosphor layer 3 is preferably 30 nm or smaller, and more preferably 20 nm or smaller. It is desirable that the thickness of the phosphor layer 3 is adjusted to be in a range in which the change in freshness can be easily observed in accordance with change in a released amount of a chemical component (hereinafter, referred to as an objective component) expected to be released due to spoilage or degradation of fresh food. The thickness of the phosphor layer 3 can be measured by, for example, a transmission electron microscopy (TEM).

Here, the "objective component" will be described for an example. The fresh food can release one or more kinds of objective components into a gas phase when spoiled or degraded. Examples of the objective component include acidic components such as aldehydes and carboxylic acids, alcohols, basic components such as ammonia and amines, esters, and ketones. The aldehydes include, for example, hexanal, 3-methylbutanal, nonanal, isovaleraldehyde, or a mixture thereof. The carboxylic acids include, for example, formic acid, acetic acid, isovaleric acid, or a mixture thereof. The amines include, for example, trimethylamine, dimethylamine, 1,2-ethylenediamine, 1,3-propanediamine, 1,4-butanediamine, 1,5-pentanediamine, 1,6-hexanediamine, spermidine, spermine, histamine, tryptamine, or a mixture thereof. The alcohols include, for example, ethanol, isopropyl alcohol, 3-methyl-1-butanol, 1-pentanol, 1-butanol, or a mixture thereof. Esters include, for example, ethyl acetate, methyl acetate, ethyl propionate, or a mixture thereof. Ketones include, for example, methyl ethyl ketone, acetone, mercaptoacetone, or a mixture thereof.

The aggregation-induced phosphor 3a may form the phosphor layer 3 as a granular layer as shown in FIG. 2, or may form the phosphor layer 3 as a continuous film having no gap. In the phosphor layer 3 as the granular layer, each depicted granule contains a plurality of molecules of the aggregation-induced phosphor 3a. The number of the molecules of the aggregation-induced phosphor 3a, located on the shortest straight line connecting each position in the particle to a granule surface is, for example, 10 or less.

The aggregation-induced phosphor 3a preferably contains a phosphor having a polar functional group. The aggregation-induced phosphor 3a containing the polar functional group tends to react with the objective component, and accuracy of a freshness evaluation using a freshness label can be improved. In addition, solubility or dispersibility in water tends to be high. The polar functional group may be an acidic functional group or a basic functional group. Examples of the acidic functional group can include a carboxyl group and a sulfo group. Examples of the basic functional group can include a hydroxyl group and an amino group. The aggregation-induced phosphor 3a may contain a plurality of kinds of the acidic functional groups or the basic functional groups. The aggregation-induced phosphor 3a preferably contains two or more carboxyl groups in one molecule.

As the aggregation-induced phosphor 3a, a tetraphenylethylene skeleton represented by Structural Formula (2), a silole skeleton represented by Structural Formula (3), or a phosphoryl oxide skeleton represented by Structural Formula (4) can be used. Each of the compounds may be a cis-form, a trans-form, or a mixture of a cis-form and a trans-form.

(2)

(3)

(4)

The aggregation-induced phosphor 3a preferably includes a tetraphenylethylene derivative represented by Formula (I) below. The compound represented by Formula (I) below is excellent in reactivity with the objective component.

(I)

In the Formula (I), $F_1$, $R_2$, $R_3$, and $R_4$ are each independently selected from the group consisting of:
$L_1M_1$, —$(CH_2)_m$-$L_2M_2$, —X—$(CH_2)_n$-$L_3M_3$, —Y—$(CH_2)_o$—Z—$(CH_2)_p$-$L_4M_4$ (where, $L_1$, $L_2$, $L_3$, and $L_4$ each independently represent one of —$CO_2$— or —$SO_3$—; $M_1$, $M_2$, $M_3$, and $M_4$ each independently represent a hydrogen atom or a cation; X, Y, Z each independently represent one of —O—, —NH—, or —S—; and m, n, o, and p each independently represent an integer of 1 to 6), a hydrogen atom, a halogen atom, a hydroxyl group, a nitro group, a carbamoyl group, an alkyl group having 1 to 6 carbon atoms, a haloalkyl group having 1 to 6 carbon atoms, an alkenyl group having 2 to 6 carbon atoms, a cycloalkyl group having 3 to 10 carbon atoms, an alkyloxy group having 1 to 6 carbon atoms, an acyl group having 2 to 6 carbon atoms, amino group, an alkylamino group having 1 to 6 carbon atoms, an aryl group having 6 to 10 carbon atoms, and a heteroaryl group having 5 to 10 carbon atoms. Furthermore, at least two of $R_1$, $R_2$, $R_3$, and $R_4$ are independently selected from the group consisting of -$L_1M_1$, —$(CH_2)_m$-$L_2M_2$, —X—$(CH_2)_n$-$L_3M_3$, and —Y—$(CH_2)_o$—Z—$(CH_2)_p$-$L_4M_4$ (here, $L_1$, $L_2$, $L_3$, $L_4$, $M_1$, $M_2$, $M_3$, $M_4$, X, Y, Z, m, n, o, and p are the same as described above.)

Specific examples of the tetraphenylethylene derivative can include compounds represented by Structural Formulas (5), (7), (9), and (10) below.

(5)

(7)

(9)

(10)

The structure 1 for a freshness label is manufactured by, for example, the following method.

First, a treatment liquid is prepared by dissolving the aggregation-induced phosphor 3a in an organic solvent. Any kind of the organic solvent may be utilized as long as the organic solvent can dissolve the aggregation-induced phosphor 3a, an organic solvent having a low evaporation temperature is preferred. For example, ethanol is used as the organic solvent. If the compound represented by Structural Formula (7) is used, a concentration of the aggregation-induced phosphor 3a in the treatment solution is, for example, 50 μM (molality) or more and 1 mM (molality) or less.

Next, after the base material 2 is immersed in the treatment liquid to be impregnated with the treatment liquid, the base material 2 is extracted from the treatment liquid and dried. The base material 2 may be impregnated with the treatment liquid by dispensing the treatment liquid using a dropper or the like. In this manner, the structure 1 for a freshness label is obtained. The structure 1 for a freshness label typically does not include an organic solvent, because the solvent evaporates away.

Next, a freshness label including the structure 1 for a freshness label will be described.

Figure 3:
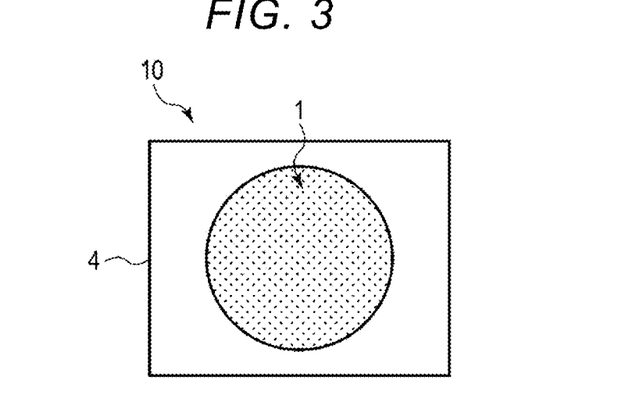
FIG. 3 schematically illustrates a top view of an example of a freshness label.

FIG. 3 schematically illustrates a top view of an example of the freshness label according to the embodiment. A freshness label 10 shown in FIG. 3 includes the structure 1 for a freshness label shown in FIG. 1, a support 4, and water.

The support 4 supports the freshness label 10 so that an atmosphere surrounding the freshness label can contact the freshness label. The support 4 need not be a porous body but may be a porous body. In the latter case, the objective component can contact the freshness label 10 via movement/diffusion through the support 4. A material of the support 4 preferably has water resistance, acid resistance, and alkali resistance. Also, the material preferably does not emit fluorescence. However, even if the material emits fluorescence, it may still be suitable as long as its fluorescence does not affect the observation of fluorescence from the structure 1 in use as a freshness label. The material of the support 4 may be the same material as the base material 2. The support 4 is, for example, a plastic sheet, paper, cloth, or sponge. The support 4 may be omitted in some examples. Also, if the support 4 is a porous body, the entirety of the structure 1 for a freshness label may be covered with the support 4.

Water is held by the structure 1 when being used as a freshness label. If the support 4 is the porous body, some of the water may be held by the structure 1 for a freshness label and other water may be held by the support 4. In the freshness label 10, the mass of the water relative to the mass of the aggregation-induced phosphor 3a is, for example, 0.5 or more.

When manufacturing the freshness label 10, first, the structure 1 is immersed in water to be impregnated with water, and then extracted from the water. The structure 1 may be impregnated with water by dispensing water using a dropper or the like, or may be caused to contain the water by exposing the structure 1 to water vapor. Distilled water, purified water, ion-exchanged water, or a mixture thereof can be used.

The structure 1 after being extracted from the water is attached to the support 4 using a bonding member such as an adhesive or an adhesive tape. Alternatively, a cut, slot, or a through hole may be provided on a part of the support 4, and the structure 1 for a freshness label may be fitted and fixed to the cut, slot, or through hole. In this manner, the freshness label 10 shown in FIG. 3 is obtained. In some examples, the structure 1 and the support 4 may be integrated with each other, and then immersed in water to obtain the freshness label 10.

As described above, the freshness label 10 according to the embodiment includes the structure 1 (and water) supported on the base material 2. Any content of the water may be used, as long as, at the content, the initial fluorescence of the freshness label 10 becomes weak or non-fluorescent. That is, the structure 1 for a freshness label becomes weak or non-fluorescent when containing the water of whatever amount. Without being limited to any particular mechanism, the present inventors consider one possible mechanism is as follows.

Figure 4:
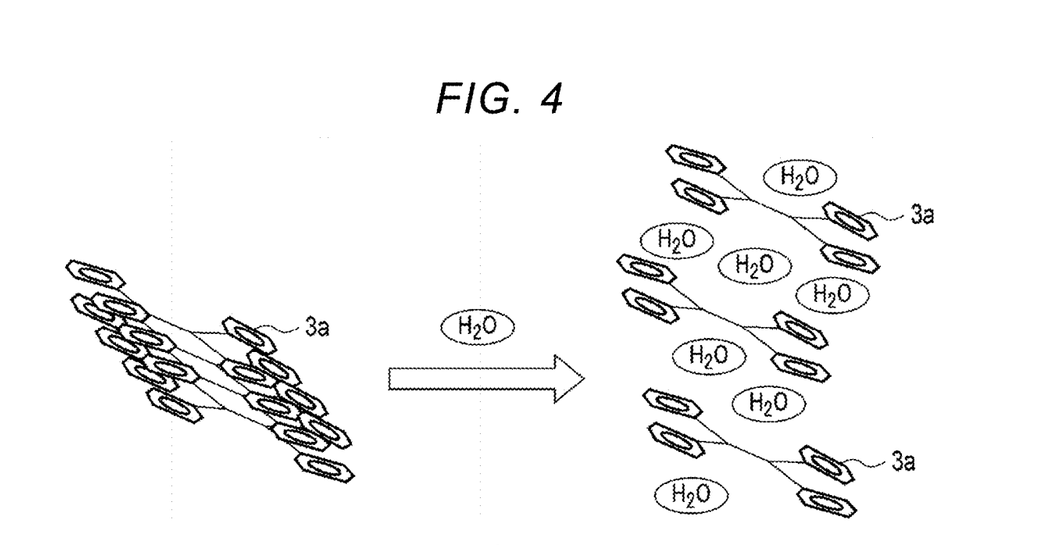
FIG. 4 illustrates a quenching mechanism of an aggregation-induced phosphor.

FIG. 4 illustrates an example of a quenching mechanism of the aggregation-induced phosphor. As shown in FIG. 4, if an aggregate of the molecules of the aggregation-induced phosphor 3a and water come into contact with each other, water molecules enter gaps between the molecules of the aggregation-induced phosphor 3a, and a distance between the molecules increases. Alternatively, if the aggregate of the molecules of the aggregation-induced phosphor 3a and the water come into contact with each other, conformation of the molecules of the aggregation-induced phosphor 3a changes. If arrangement of the molecules of the aggregation-induced phosphor 3a changes, the fluorescence of the aggregation-induced phosphor 3a is weakened.

In the structure 1 shown in FIG. 2, almost no water is present, and thus the molecules of the aggregation-induced phosphor 3a form a layered structure. The aggregation-induced phosphor 3a in which the molecules are arranged as described above can emit fluorescence with relatively high intensity. On the other hand, since the freshness label 10 is impregnated with water, water molecules enter the gaps between the molecules of the aggregation-induced phosphor 3a. Therefore, the freshness label 10 emits fluorescence at an intensity weaker than that of the dry or initial structure 1 or even does not emit fluorescence.

In particular, the aggregation-induced phosphor 3a containing a polar functional group, such as a carboxyl group, has a high affinity with water. Therefore, it is considered that the aggregation-induced phosphor 3a containing a polar functional group is more likely to become weak or non-fluorescent by adding water. Formula (II) below shows an ionization reaction of the aggregation-induced phosphor having a carboxyl group (TPE-COOH). This reaction is an equilibrium reaction.

$$\text{TPE-COOH} \Leftrightarrow \text{TPE-COO}^- + \text{H}^+ \quad \text{(II)}$$

Figure 5:
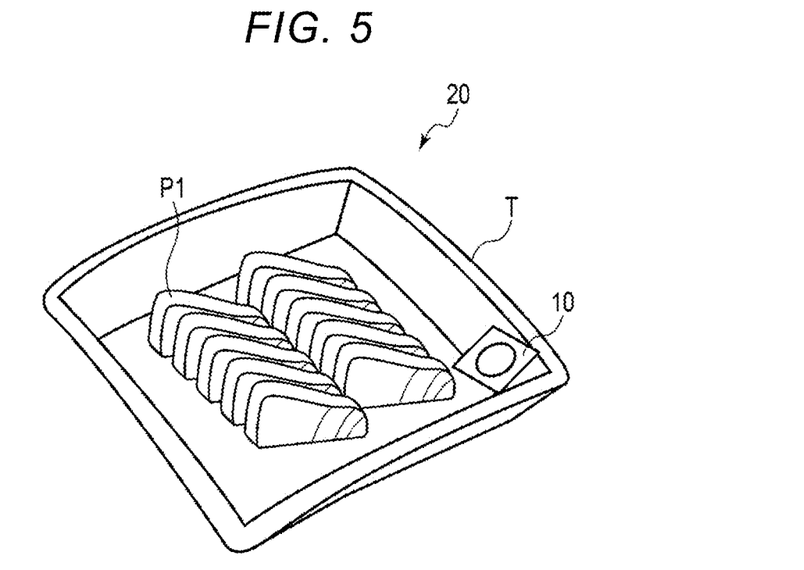
FIG. 5 illustrates a perspective view of an example of packaged food including the freshness label.

The freshness label 10 is disposed, for example, near food such as fresh food, and is used in an airtight space with the food. FIG. 5 shows an example of a method for using the freshness label 10. FIG. 5 illustrates a perspective view of an example of packaged food including the freshness label according to the embodiment. Packaged food 20 shown in FIG. 5 includes the freshness label 10, food P1, a tray T supporting the freshness label 10 and the food P1, and a wrap film (not shown). The freshness label 10 and the food P1 are enclosed airtightly with the tray T and the wrap film so as not to come into contact with the outside air. That is, the tray T and the wrap film form an airtight container. The freshness label 10 and the food P1 are enclosed in the airtight container. The freshness label 10 may be placed on the tray T as shown in FIG. 5, or may be attached to an inner surface of the wrap film.

A kind of the food P1 is not specified, and the freshness label 10 is suitably used as a freshness label for food containing water, such as marine products and livestock products.

As described below, in the packaged food 20, freshness of the food P1 can be quantified by irradiating the freshness label 10 with excitation light such as ultraviolet rays and measuring the intensity (brightness) of the fluorescence. Here, as an example, it is assumed that in the food P1, the objective component generated along with a decrease in freshness is an acidic component and the aggregation-induced phosphor 3a contains an acidic functional group as a polar functional group.

If the food P1 is in a fresh state, a concentration of the objective component in an atmosphere in the airtight container is low. In this case, the objective component has a small effect on the arrangement of molecules of the aggregation-induced phosphor 3a. Therefore, in this case, the aggregation-induced phosphor 3a does not emit fluorescence with a high intensity even if irradiated with excitation light.

If the freshness of the food P1 decreases, the concentration of the objective component in the atmosphere in the airtight container increases. If the concentration of the objective component in the atmosphere increases, a part of the objective component is dissolved in water contained in the freshness label 10. Since this aqueous solution has the same polarity as the polar functional group of the aggregation-induced phosphor 3a, if the concentration of the objective component in the aqueous solution increases, the affinity or solubility of the aggregation-induced phosphor 3a with and in the aqueous solution decreases. Therefore, if the concentration of the objective component in the atmosphere increases, the molecular arrangement of the aggregation-induced phosphor 3a approaches a state where no water is present. Therefore, it is considered that if the freshness of the food P1 decreases, the intensity of the fluorescence emitted from the aggregation-induced phosphor 3a by irradiation with the excitation light increases.

For example, an ultraviolet (UV) lamp is used to irradiate the freshness label 10 with the excitation light. A wavelength of the ultraviolet rays varies depending on the kind of the aggregation-induced phosphor 3a. According to an example, the wavelength is 350 nm or more and 530 nm or less. Also, as described above, a photodetector or an image pickup device is used for measuring the fluorescence intensity, for example. For example, first, a fluorescent image is captured using a digital camera or the like while irradiating the freshness label 10 with a UV lamp. Then, using image processing software, each gradation value of RBG of the fluorescence image is obtained. The fluorescence intensity of the freshness label 10 can be quantified using these gradation values. For example, an arithmetic average of these gradation values can be used as the fluorescence intensity.

As described above, if aggregation-induced phosphor 3a having an acidic functional group is used and the objective component is an acidic component, the fluorescence of the freshness label 10 becomes higher as the concentration of the objective component increases. On the other hand, if the aggregation-induced phosphor 3a having a basic functional group is used and the objective component is a basic component, the fluorescence of the freshness label 10 becomes higher as the concentration of the objective component increases.

As described below, if the freshness label 10 is used, freshness of the food P1 can be quantified by a simple method for irradiating the freshness label 10 with excitation light such as ultraviolet rays and measuring the intensity (brightness) of the fluorescence. Moreover, the freshness can be quantified with high accuracy. The reason will be described below.

As described above, the food P1 for which the freshness label 10 is desired to be used, such as fresh food, generally has a large content of water. Therefore, water vapor pressure in the airtight container increases over time and eventually reaches a saturated water vapor pressure.

If a freshness label containing a solution in which the aggregation-induced phosphor is dissolved in an organic solvent is used, the water content of the freshness label is small immediately after the freshness label is enclosed in the airtight container, and increases over time, although the water content reaches finally almost constant value. The reason is that the increase in water vapor pressure caused by the release of water into the gas phase by the fresh food enclosed in the airtight container together with the freshness label continues until the water vapor pressure reaches the saturated water vapor pressure. If the water content of the freshness label increases, as described above, the arrangement of the molecules of the aggregation-induced phosphor changes. As a result, the fluorescence intensity of the freshness label changes. Therefore, in the freshness label using the organic solvent, the magnitude of the effect of water on the fluorescence intensity changes during the period from enclosing the freshness label in the airtight container until the water vapor pressure reaches the saturated water vapor pressure. Therefore, if such a freshness label is used, the freshness could not be accurately evaluated.

The freshness label according to the embodiment contains water. Food, such as fresh food, releases water into the gas phase. Therefore, a difference between the amount of water evaporating from the freshness label and the amount of water supplied to the freshness label from the gas phase is relatively small, during the period from enclosing the freshness label in the airtight container until the water vapor pressure reaches the saturated water vapor pressure. After the water vapor pressure reaches the saturated water vapor pressure, the amount of water evaporating from the freshness label is equal to the amount of water supplied to the freshness label from the gas phase. Therefore, the water content of the freshness label is maintained to be substantially constant after being enclosed in the airtight container. Therefore, with the freshness label according to the embodiment, the change in the fluorescence intensity caused by a change in the water content hardly occurs. Therefore, if the freshness label is used, only a substance which is generated by decomposition or deterioration of components contained in food and is diffused into the gas phase appreciably affects the fluorescence intensity.

As described above, the freshness label according to the embodiment can achieve simple and accurate freshness evaluation. Furthermore, if the freshness label according to the embodiment is used, it is possible to achieve not only a simple detection of the presence or absence of the objective component, but also evaluate the concentration and a K value of the objective component. That is, the fluorescence intensity of the freshness label according to the embodiment can show a positive correlation to the concentration and the K value of the objective component.

The K value is one of the indices indicating the freshness of food, and a large K value indicates that the freshness is low. The K value is calculated from the number of decomposition products generated from a nucleic acid-related substance over time.

Figure 6:
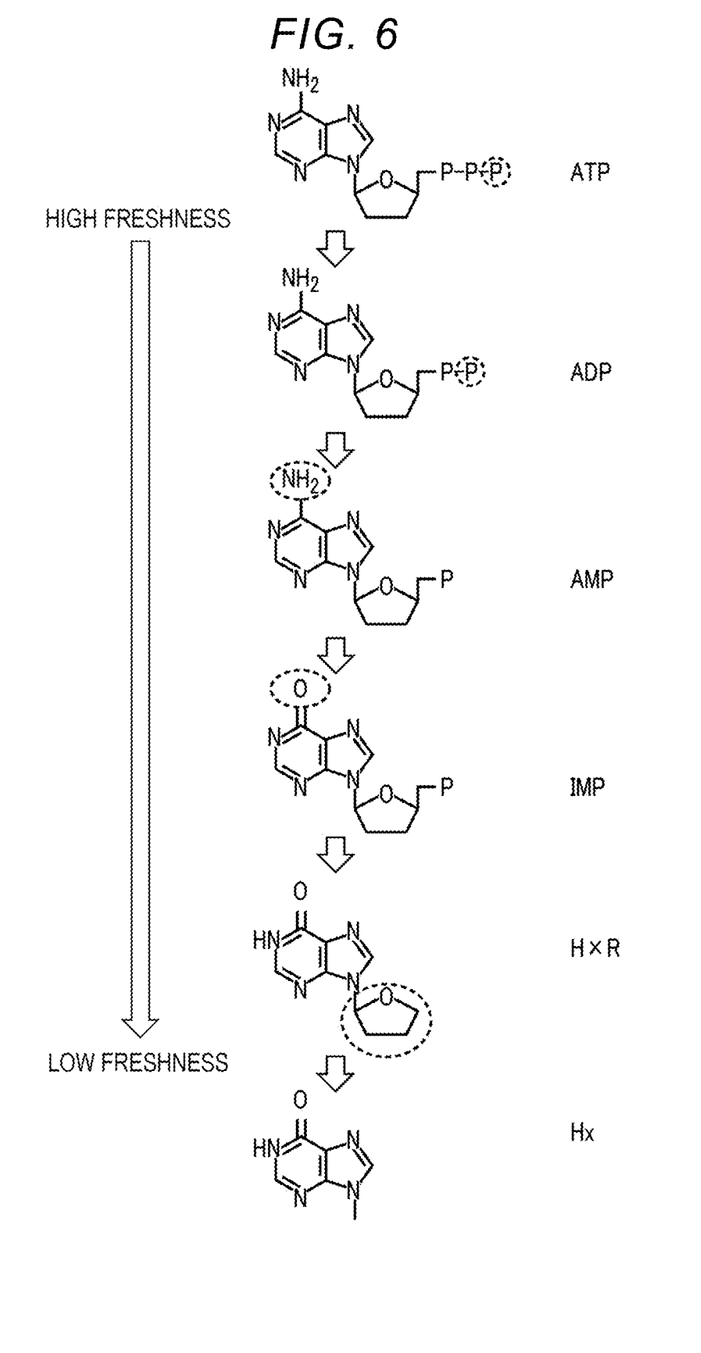
FIG. 6 illustrates a degradation process of a nucleic acid-related substance.

FIG. 6 illustrates a degradation process of the nucleic acid-related substance. As shown in FIG. 6, adenosine triphosphate (ATP) contained in food is decomposed into adenosine diphosphate (ADP). ADP is decomposed into adenosine monophosphate (AMP). AMP is decomposed into inosine monophosphate (IMP). IMP is decomposed into inosine (HxR). HxR is decomposed into hypoxanthine (Hx). ATP, ADP, AMP, and IMP are substances contained in food with high freshness, and HxR and Hx are substances contained in food with low freshness.

Figure 7:
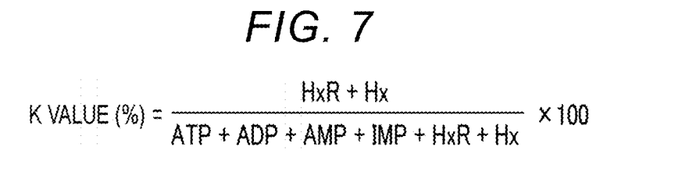
FIG. 7 is an equation employed to calculate a K value.

FIG. 7 is an equation employed to calculate the K value. As shown in FIG. 7, the K value is a value indicating a proportion of the total amount of HxR and Hx to the total amount of ATP, ADP, AMP, IMP, HxR, and Hx, as a percentage. The amounts of ATP, ADP, AMP, IMP, HxR, and Hx in the food are calculated by, for example, high performance liquid chromatography or electrophoresis. In general, if the K value is 60% or more, the food is determined to be spoiled. Evaluation using the K value can show the freshness of the food relatively accurately. However, in order to calculate the K value, it is necessary to collect a sample from food. Also, it is necessary to use an expensive analytical instrument.

As described above, the fluorescence intensity of the freshness label according to the embodiment has a positive correlation with the concentration of the objective component. The concentration of the objective component has a positive correlation with the K value. Therefore, if the fluorescence intensity of the freshness label is converted to numerical values and a calibration curve representing the relationship between the numerical value and the concentration of the objective component or the K value is prepared in advance, the concentration of the objective component in the gas phase and/or the K value of the food can be obtained by measuring the fluorescence intensity and referencing the measurement result to the calibration curve.

Figure 8:
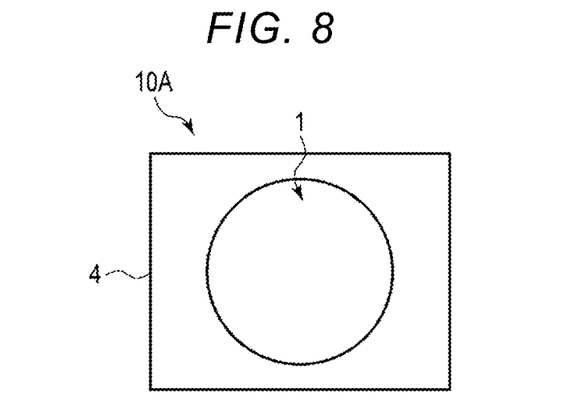
FIG. 8 schematically illustrates a top view of another example of the freshness label.

Next, another method for using the freshness label according to the embodiment will be described. FIG. 8 schematically illustrates a top view of another example of the freshness label according to the embodiment. A freshness label 10A shown in FIG. 8 has the same structure as the freshness label 10 shown in FIG. 3, except further including an acid. That is, the freshness label 10A shown in FIG. 8 includes the structure 1 for a freshness label according to the embodiment, the support 4, water, and an acid. The water and the acid are supported by the structure 1. In other words, the structure 1 supports (e.g., retains) an acidic aqueous solution. As the acid, for example, formic acid, hydrochloric acid, acetic acid, or a mixture thereof is used. As the acid, it is preferable to use the acetic acid, from a viewpoint of safety. Also, the polar functional group of the aggregation-induced phosphor 3a is preferably an acidic functional group. Here, as an example, it is assumed that the polar functional group of aggregation-induced phosphor 3a is an acidic functional group.

The freshness label 10A shown in FIG. 8 is obtained, for example, by exposing the freshness label 10 shown in FIG. 3 to a vapor containing a high concentration of acid. The acid content in the freshness label 10A can be adjusted according to the desired fluorescence intensity.

It is considered that since the freshness label 10A shown in FIG. 8 contains an acid, the molecular arrangement of aggregation-induced phosphor 3a is close to a state without containing water or the conformation of aggregation-induced phosphor 3a changes due to the presence of an acid component. Therefore, the freshness label 10A shows fluorescence stronger than the freshness label 10 shown in FIG. 3.

If the freshness label 10A contacts a basic objective component, the fluorescence intensity of the freshness label 10A decreases. If the freshness label 10A contacts a certain amount of the basic objective component, the fluorescence intensity thereof becomes non-fluorescent. That is, the fluorescence intensity of the freshness label 10A shown in FIG. 8 may show a negative correlation with the concentration of the objective component and the K value. Therefore, as in the case of the freshness label 10 shown in FIG. 3, if the fluorescence intensity of the freshness label 10A is converted to numerical values and a calibration curve representing the relationship between the numerical value and the concentration of the objective component or the K value is prepared in advance, the concentration of the objective component in the gas phase or the K value of the food can be obtained by measuring the fluorescence intensity and referencing the measurement result to the calibration curve.

The structure 1 may be distributed without water or the like therein, and then caused to contain water or the like at a site where the label is to be enclosed in an airtight container together with the food P1. In this case, the structure 1 may be distributed as a freshness label kit including the structure 1 for a freshness label and one or more liquids to be included therein, that is, water, acid, or a combination of water and acid. If the combination of water and an acid is included in the freshness label kit, the water and the acid may be contained in separate containers, or may be mixed to be contained in a single container as an aqueous solution.

Alternatively, the freshness label 10 or 10A in which water or the like is contained in the structure 1 may be distributed to be enclosed in an airtight container together with the food P1.

The structure for a freshness label according to the embodiment described above includes the phosphor layer fixed to the base material. Therefore, the freshness label can be prepared simply by impregnating the structure 1 with water. Since the freshness label containing water is not easily affected by water in the gas phase, the freshness of food can be evaluated with higher accuracy than a freshness label containing an organic solvent.

EXAMPLES

1. Example of Using Acetic Acid as Objective Component

The freshness label 10 shown in FIG. 3 was prepared by the following method. First, the aggregation-induced phosphor 3a was dissolved in ethanol to prepare a treatment solution. After the base material 2 was immersed in the treatment liquid, the base material 2 was extracted from the treatment liquid, placed on a glass plate, and dried. As the aggregation-induced phosphor 3a, a compound represented by the above Structural Formula (5) was used. As the base material 2, a circular glass fiber filter was used. In this manner, the structure 1 for a freshness label shown in FIG. 1 was obtained. In the structure 1 for a freshness label, the phosphor layer 3 provided on a surface of the glass fiber was observed by TEM. As a result, the thickness of the phosphor layer 3 was 20 nm. The structure 1 for a freshness label was observed while irradiating the structure with ultraviolet rays from a UV lamp. As a result, it was found that strong fluorescence was emitted. The wavelength of the ultraviolet rays with which the structure is irradiated by the UV lamp was 365 nm. In addition, in this case, the structure 1 was imaged using a digital camera, and digital image data was recorded.

Then, the structure 1 was immersed in pure water, and then extracted from the pure water, and the base material 2 was impregnated with water. In this manner, the freshness label 10 shown in FIG. 3 was obtained. The support 4 was omitted. Hereinafter, the freshness label in this example is referred to as a freshness label R1. The freshness label R1 was observed while irradiating the label with ultraviolet rays from a UV lamp. As a result, it was found that the freshness label R1 was non-fluorescent. In addition, in this case, the freshness label R1 was imaged using a digital camera, and digital image data was recorded.

Then, the two freshness labels R1 were placed in a container in which acetic acid water vapor was enclosed airtightly and a container in which pure water vapor was enclosed airtightly, respectively, and were exposed to vapor of acetic acid water and pure water. As the acetic acid water, a mixed solution of 20 µL of acetic acid and 200 µL of water was used. In addition, 1 g of pure water was stored in each of the airtight containers for moisturizing. As the container, a plastic airtight container with a capacity of about 100 mL was used. A circular freshness label R1 having a diameter of 021 mm was placed in the container with a gap so as not to be directly wet with acetic acid water or water.

After one hour, the freshness label R1 was picked up from each container, and observed while irradiating the label with ultraviolet rays from a UV lamp to examine the fluorescence intensity. As a result, the freshness label R1 placed in the container in which the acetic acid water vapor was enclosed airtightly showed the same fluorescence intensity as the structure 1 for a freshness label. On the other hand, the freshness label R1 placed in the container in which the pure water vapor was enclosed airtightly remained non-fluorescent. In addition, in this case, the freshness label R1 was imaged using a digital camera, and digital image data was recorded.

Figure 9:
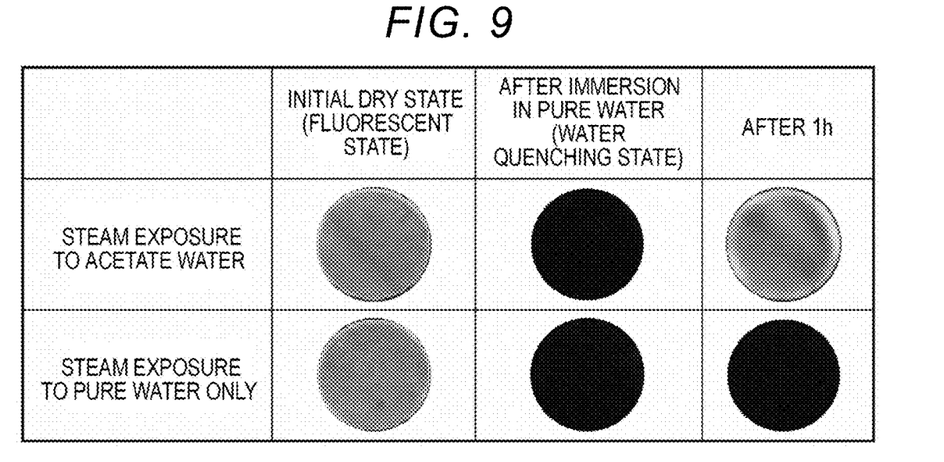
FIG. 9 is a table summarizing images obtained in a particular example in which an acetic acid is used as an objective component.

FIG. 9 is a table summarizing images obtained in this example in which an acetic acid is used as an objective component. From FIG. 9, it can be seen that the fluorescence intensity of the freshness label R1 is not affected by pure water, and is affected only by acetic acid water. Therefore, if the freshness label R1 is used, freshness can be quantified with high accuracy if acetic acid is used as the objective component.

2. Example of Using Trimethylamine as Objective Component

First, the freshness label R1 was produced by the same method as above. The freshness label R1 was enclosed in the container in which acetic acid water vapor was enclosed airtightly, and exposed to acetic acid water vapor for a sufficient time to obtain the freshness label 10A shown in FIG. 8. Hereinafter, this freshness label 10A is referred to as a freshness label R2. As the acetic acid water, a mixed solution of 20 µL of acetic acid and 200 µL of water was used. In addition, 1 g of pure water was stored in the airtight container for moisturizing. The freshness label R2 was observed while irradiating the label with ultraviolet rays from a UV lamp. As a result, it was found that strong fluorescence was emitted. In addition, in this case, the freshness label R2 was imaged using a digital camera, and digital image data was recorded.

Then, the two freshness labels R2 were placed in a container in which trimethylamine water vapor was enclosed airtightly and a container in which pure water vapor was enclosed airtightly, respectively, and were exposed to trimethylamine water vapor and pure water vapor. As the trimethylamine water, a mixed solution containing 10 µL of trimethylamine, 30 µL of ethanol, and 160 µL of water was used. In addition, 1 g of pure water was stored in each of the airtight containers for moisturizing.

After one hour, the freshness label R2 was taken out of each container, and observed while irradiating the label with ultraviolet rays from a UV lamp to examine the fluorescence intensity. As a result, the fluorescence intensity of the freshness label R2 placed in the container in which the trimethylamine water vapor was enclosed airtightly was significantly lowered relative to the fluorescence intensity before the test. On the other hand, the fluorescence intensity of the freshness label R2 placed in the container in which the pure water vapor was enclosed airtightly was almost equal to the fluorescence intensity before the test. In addition, in this case, the freshness label R2 was imaged using a digital camera, and digital image data was recorded.

Figure 10:
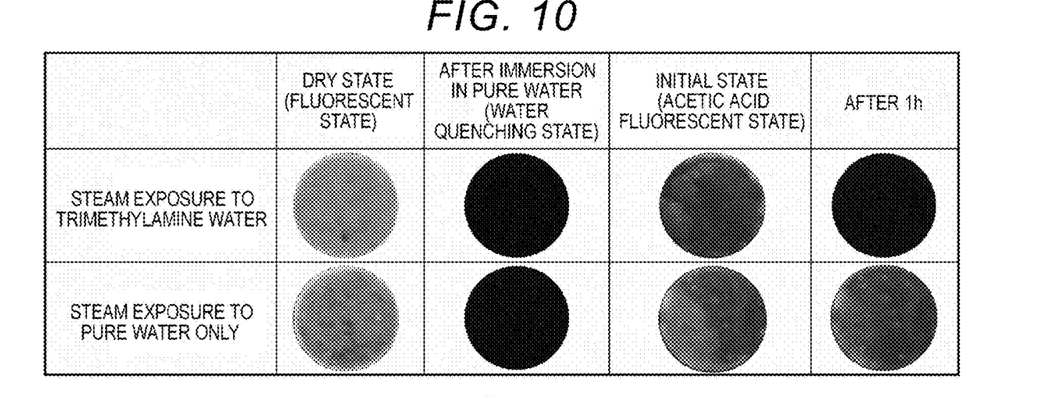
FIG. 10 is a table summarizing images obtained in a particular example in which trimethylamine is used as an objective component.

FIG. 10 is a table summarizing images obtained in in this example in which trimethylamine is used as an objective component. From FIG. 10, it can be seen that the fluorescence intensity of the freshness label R2 is not affected by pure water, and is affected only by the trimethylamine water. Therefore, if the freshness label R2 is used, freshness can be quantified with high accuracy if trimethylamine is used as the objective component.

3. Example of Using Fresh Fish

Figure 11:
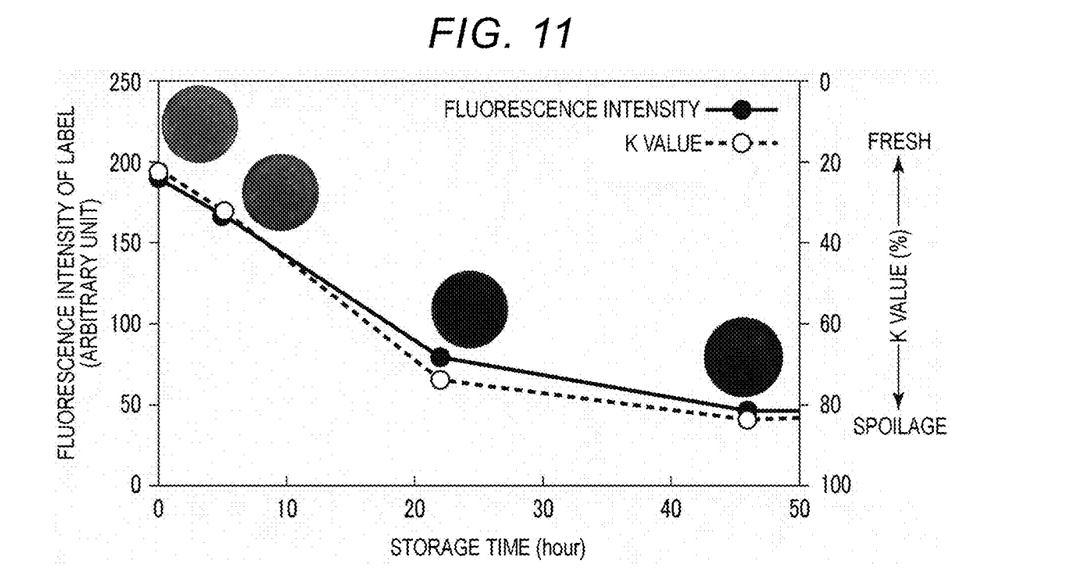
FIG. 11 is a graph showing an example of a relationship between storage time of a horse mackerel and a fluorescence intensity and a K value of the freshness label.

First, the packaged food 20 shown in FIG. 5 was prepared. As the food P1, horse mackerel was used. The freshness label R2 was used as the freshness label 10. The packaged food 20 was stored in an environment at 25° C., and the fluorescence intensity of the freshness label R2 and the K value were measured at each storage time shown in Table 1 below. A gradation value of RBG was calculated using image processing software based on the image data obtained when irradiating the freshness label with ultraviolet rays from a UV lamp, and an arithmetic average thereof was obtained to convert the fluorescence intensity to a numerical value. Also, the K value was obtained by collecting a part of the horse mackerel and using an electrophoresis method. The results thereof are shown in FIG. 11. In the electrophoresis method, the measurement was performed using a freshness checker manufactured by QS-Solution.

FIG. 11 is a graph showing an example of a relationship between storage time of a horse mackerel and a fluorescence intensity and a K value of the freshness label. As shown in FIG. 11, a high correlation was observed between the fluorescence intensity of the freshness label and the K value. Therefore, if the freshness label R2 is used, freshness of the horse mackerel can be evaluated with high accuracy. In the horse mackerel sample used in the test, an odor component was found using a gas chromatograph. As a result, trimethylamine was detected from the sample in which the freshness of the horse mackerel was degraded. In addition, an approximate K value could be obtained by converting the fluorescence intensity of the freshness label R2 to a numerical value and generating a calibration curve.

4. Comparison with Freshness Label Utilizing an Organic Solvent

First, the aggregation-induced phosphor was dissolved in an organic solvent to prepare a treatment solution. As the organic solvent, a mixture of polyethylene glycol dimethyl ether and ethanol was used. The base material was immersed in the treatment liquid, and then the base material was extracted from the treatment liquid. Thereafter, the ethanol content was dried off and the base material was impregnated with the treatment liquid containing almost only the polyethylene glycol dimethyl ether as a solvent. As the polyethylene glycol dimethyl ether, High Solve MPM (trade name, manufactured by Toho Chemical Industry Co., Ltd.) was used. As the aggregation-induced phosphor, a compound represented by the above Structural Formula (5) was used. As the base material, a circular glass fiber filter was used. In this manner, the freshness label according to a comparative example was obtained.

Hereinafter, the freshness label is referred to as a freshness label R3. The freshness label R3 was observed while irradiating the label with ultraviolet rays from a UV lamp. As a result, it was found that the freshness label R1 was almost non-fluorescent. In addition, in this case, the freshness label R3 was imaged using a digital camera, and digital image data was recorded.

Next, performances of freshness label R2 and freshness label R3 were compared to each other.

The freshness label R2 was exposed to trimethylamine water, after a state of emitting fluorescence was found by exposing the freshness label to acetic acid water in the same procedure as in <2. Example of using trimethylamine as objective component>. The freshness label R3 was also exposed to trimethylamine water. As a comparison object for the trimethylamine water, only pure water was used for exposure. 1 g of pure water was stored in each of the airtight containers for moisturizing. As the acetic acid water, a mixed solution of 20 µL of acetic acid and 200 µL of water was used. As the trimethylamine water, a mixed solution containing 10 µL of trimethylamine, 30 µL of ethanol, and 160 µL of water was used. The results are shown in FIG. 12.

Figure 12:
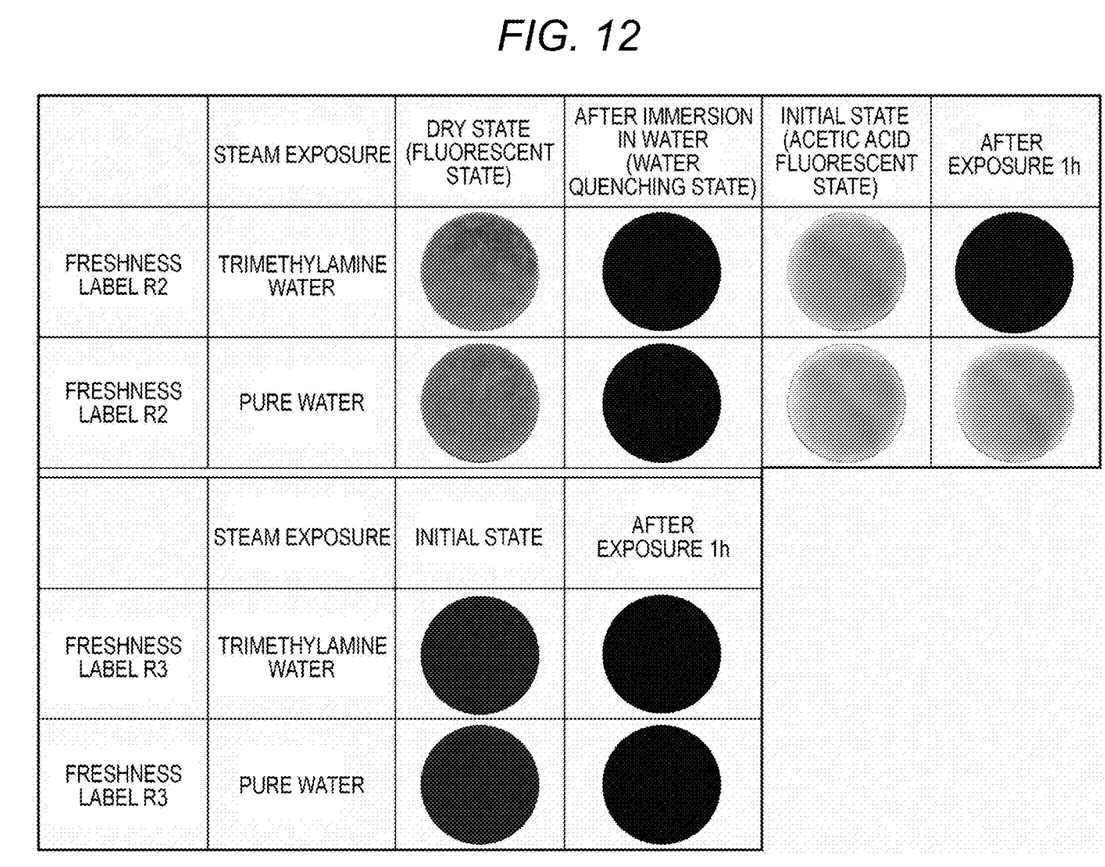
FIG. 12 is a table summarizing images obtained in in a particular example embodiment and Comparative Example in which trimethylamine is used as an objective component.

FIG. 12 is a table summarizing images obtained in Example and Comparative Example in which trimethylamine is used as an objective component. As shown in FIG. 12, in the freshness label R2, the quenching effect upon exposure to trimethylamine from the fluorescent state of acetic acid was remarkable. On the other hand, if the freshness label was exposed only to pure water, the initial fluorescent state was maintained. On the other hand, the freshness label R3 was almost non-fluorescent at the initial state, and maintained the quenched state even if the freshness label was exposed to triethylamine, as in the case of exposure only to pure water.

That is, it was found that under the condition that a large amount of water was present, the expression of fluorescence was suppressed in the freshness label R3 even if the amine component was present. On the other hand, the freshness label R2 succeeded in detecting the presence of trimethylamine without being affected by a large amount of water, and the difference in the effectiveness of the freshness label R2 and the freshness label R3 could be found.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for identifying a freshness level of a food product with a freshness label including a freshness label structure that can retain water therein, the freshness label structure including a base material and a phosphor layer including an aggregation-induced phosphor that is held on a surface of the base material, the method comprising:
   immersing the freshness label in an aqueous solution or water; and
   after said immersing, packing the food product along with the freshness label in a sealed container.

2. The method according to claim 1, wherein the phosphor layer is quenchable with water.

3. The method according to claim 1, wherein the base material has a porous structure.

4. The method according to claim 1, wherein the base material has a mesh structure.

5. The method according to claim 1, wherein the aggregation-induced phosphor comprises a phosphor having a polar functional group.

6. The method according to claim 5, wherein the polar functional group includes an acidic functional group.

7. The method according to claim 5, wherein the polar functional group includes a basic functional group.

8. The method according to claim 1, wherein the aggregation-induced phosphor includes a tetraphenylethylene derivative represented by:

wherein, in the formula, $R_1$, $R_2$, $R_3$, and $R_4$ are each independently selected from a group consisting of:
$L_1M_1$,
$(CH_2)_m\text{-}L_2M_2$,
$X\text{—}(CH_2)_n\text{-}L_3M_3$,
$Y\text{—}(CH_2)_o\text{—}Z\text{—}(CH_2)_p\text{-}L_4M_4$,
a hydrogen atom,
a halogen atom,
a hydroxyl group,
a nitro group,
a carbamoyl group,
an alkyl group having 1 to 6 carbon atoms,
a haloalkyl group having 1 to 6 carbon atoms,
an alkenyl group having 2 to 6 carbon atoms,
a cycloalkyl group having 3 to 10 carbon atoms,
an alkyloxy group having 1 to 6 carbon atoms,
an acyl group having 2 to 6 carbon atoms,
amino group, an alkylamino group having 1 to 6 carbon atoms,
an aryl group having 6 to 10 carbon atoms, and
a heteroaryl group having 5 to 10 carbon atoms, where
  $L_1$, $L_2$, $L_3$, and $L_4$ each independently represent —$CO_2$— or —$SO_3$—;
  $M_1$, $M_2$, $M_3$, and $M_4$ each independently represent a hydrogen atom or a cation;
  X, Y, Z each independently represent —O—, —NH—, or —S—; and
  m, n, o, and p each independently represent an integer of 1 to 6; and
at least two of $R_1$, $R_2$, $R_3$, and $R_4$ are selected from -$L_1M_1$, —$(CH_2)_m$-$L_2M_2$, —X—$(CH_2)_n$-$L_3M_3$, and —Y—$(CH_2)_o$—Z—$(CH_2)_p$-$L_4M_4$.

9. The method according to claim 1, wherein the freshness label is immersed in water.

10. The method according to claim 1, wherein the freshness label is immersed in the acidic aqueous solution.

* * * * *